(12) United States Patent
Mao et al.

(10) Patent No.: US 6,919,431 B1
(45) Date of Patent: Jul. 19, 2005

(54) POLYPEPTIDE-HUMAN SNARE PROTEIN 25 AND A POLYNUCLEOTIDE ENCODING THE SAME

(75) Inventors: Yumin Mao, Shanghai (CN); Yi Xie, Shanghai (CN)

(73) Assignee: Shanghai Bio Road Gene Development, Ltd., Shanghai (CN)

( * ) Notice: Subject to any disclaimer, the term of this patent is extended or adjusted under 35 U.S.C. 154(b) by 354 days.

(21) Appl. No.: 10/148,125

(22) PCT Filed: Nov. 20, 2000

(86) PCT No.: PCT/CN00/00477

§ 371 (c)(1), (2), (4) Date: May 28, 2002

(87) PCT Pub. No.: WO01/38390

PCT Pub. Date: May 31, 2001

(30) Foreign Application Priority Data

Nov. 26, 1999 (CN) .......................... 99124120 A

(51) Int. Cl.[7] .......................... C07K 1/00; C07K 14/00; C07K 17/00
(52) U.S. Cl. ..................................... 530/350
(58) Field of Search ................. 530/350; 435/69.1, 435/7.1; 514/12; 536/23.1

(56) References Cited

FOREIGN PATENT DOCUMENTS

WO 99/36523 7/1999

OTHER PUBLICATIONS

Antonin et al. NCBI Submission Accession No. AF262222.*
Antonin et al. The SNARE Vita 1alpha–beta is localized to small synaptic vesicles and participates in novel SNARE complex, Aug. 2001, The j. of Neuro Sci. vol. 20, No. 15, pp. 5724–5732.*

* cited by examiner

Primary Examiner—Robert A. Wax
Assistant Examiner—Robert B. Mondesi
(74) Attorney, Agent, or Firm—Crowell & Moring LLP

(57) ABSTRACT

The present invention discloses a novel polypeptide-Human SNARE protein 25 and polynucleotide encoding the same, as well as a method of producing the polypeptide by DNA recombinant technology. The present invention also discloses methods of using the polypeptide in treatment of various diseases, such as malignant tumor, blood disease, HIV infection, immunological disease and various inflammations. The present invention also discloses an antagonist against the polypeptide and the therapeutic use of the same. The present invention also discloses the use of such polynucleotide encoding Human SNARE protein 25.

3 Claims, 1 Drawing Sheet

Identity = 206/224 (91%), Similarity = 210/224 (93%)

```
Human SNARE       1 MSSDFEGYEQDFAVLTAEITSKIARVPRLPPDEKKQMVANVEKQLEEAKELLEQMDLEVR   60
protein 25:         MSSDFEGYEQDFAVLTAEITSKIARVPRLPPDEKKQMVANVEKQLEEA+ELLEQMDLEVR
SNARE-29KD in rat 1 MSSDFEGYEQDFAVLTAEITSKIARVPRLPPDEKKQMVANVEKQLEEARELLEQMDLEVR   60
Golgi complex:

Human SNARE      61 EIPPQSRGMYSNRMRSYKQEMGKLETDFKRSRIAYSDEVRNELLGDDGNSSENQLIKLRE 120
protein 25:         EIPPQSRGMYSNRMRSYKQEMGKLETDFKRSRIAYSDEVRNELLGD GNSSENQ
SNARE-29KD in rat 61 EIPPQSRGMYSNRMRSYKQEMGKLETDFKRSRIAYSDEVRNELLGDAGNSSENQ------ 114
Golgi complex:

Human SNARE     121 ERAHLLDNTERLERSSRRLEAGYQIAVETEQIGQEMLENLSHDREKIQRARERLRETDAN 180
protein 25:         RAHLLDNTERLERSSRRLEAGYQIAVETEQIGQEMLENLSHDREKIQRAR+RLR+ DAN
SNARE-29KD in rat 115-RAHLLDNTERLERSSRRLEAGYQIAVETEQIGQEMLENLSHDREKIQRARDRLRDADAN 173
Golgi complex:

Human SNARE     181 LGKSSRILTGMLRRIIQNRILLVILGIIVVITILMAITFSVRRH 224
protein 25:         LGKSSRILTGMLRRIIQNRILLVILGIIVVI IL AI F V+ H
SNARE-29KD in rat 174 LGKSSRILTGMLRRIIQNRILLVILGIIVVIAILTAIAFFVKGH 217
Golgi complex:
```

Identity = 206/224 (91%), Similarity = 210/224 (93%)

```
Human SNARE            1 MSSDFEGYEQDFAVLTAEITSKIARVPRLPPDEKKQMVANVEKQLEEAKELLEQMDLEVR   60
protein 25:              MSSDFEGYEQDFAVLTAEITSKIARVPRLPPDEKKQMVANVEKQLEEA+ELLEQMDLEVR
SNARE-29KD in rat      1 MSSDFEGYEQDFAVLTAEITSKIARVPRLPPDEKKQMVANVEKQLEEARELLEQMDLEVR   60
Golgi complex:

Human SNARE           61 EIPPQSRGMYSNRMRSYKQEMGKLETDFKRSRIAYSDEVRNELLGDDGNSSENQLIKLRE  120
protein 25:              EIPPQSRGMYSNRMRSYKQEMGKLETDFKRSRIAYSDEVRNELLGD GNSSENQ
SNARE-29KD in rat     61 EIPPQSRGMYSNRMRSYKQEMGKLETDFKRSRIAYSDEVRNELLGDAGNSSENQ------  114
Golgi complex:

Human SNARE          121 ERAHLLDNTERLERSSRRLEAGYQIAVETEQIGQEMLENLSHDREKIQRARERLRETDAN  180
protein 25:               RAHLLDNTERLERSSRRLEAGYQIAVETEQIGQEMLENLSHDREKIQRAR+RLR+ DAN
SNARE-29KD in rat    115 -RAHLLDNTERLERSSRRLEAGYQIAVETEQIGQEMLENLSHDREKIQRARDRLRDADAN  173
Golgi complex:

Human SNARE          181 LGKSSRILTGMLRRIIQNRILLVILGIIVVITILMAITFSVRRH  224
protein 25:              LGKSSRILTGMLRRIIQNRILLVILGIIVVI IL AI F V+ H
SNARE-29KD in rat    174 LGKSSRILTGMLRRIIQNRILLVILGIIVVIAILTAIAFFVKGH  217
Golgi complex:
```

Fig. 1

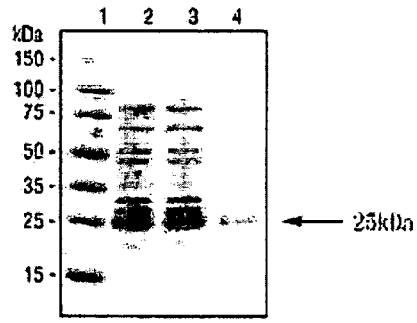

Fig. 2

POLYPEPTIDE-HUMAN SNARE PROTEIN 25 AND A POLYNUCLEOTIDE ENCODING THE SAME

FIELD OF INVENTION

The invention relates to the field of biotechnology. In particular, the invention relates to a novel polypeptide, Human SNARE protein 25, and a polynucleotide sequence encoding said polypeptide. The invention also relates to the method for the preparation and use of said polynucleotide and polypeptide.

TECHNICAL BACKGROUND

Plasma membrane plays an important role in cell life because all connections and interactions between cells and the environment must pass through the membrane. For instance, substances go into or out of a cell through the plasma membrane. Hormones and drugs act on cells via plasma membrane, and metabolism regulation, cell recognition and immunization, etc, all are related to and depend on the functions of plasma membrane.

Substances get into or out of a cell via plasma membrane. In live cells, plasma membrane is highly selective with regard to substance permeability. There are three major ways for substances to pass through plasma membrane: passive transportation, active transportation, and endocytosis and exocytosis.

Protein transportation in eukaryotes includes secretion, endocytosis, and exocytosis (Nature 1994 Nov. 3; 372 (6501): 55–63).

Macromolecules, such as proteins, polynucleotides and polysaccharides can only pass through plasma membrane via endocytosis and exocytosis. The mechanism of transporting these macromolecules is different from that of transporting small molecules such as solutes and ions, and involves the orderly formation and fusion of small vesicles along the plasma membrane. Endocytosis and exocytosis are both active transportation, because they need energy supply. One important feature of endocytosis and exocytosis is that the macromolecules are enclosed in the vesicle rather than being mixed up with other macromolecules or organelles. This ensures that macromolecules outside or inside the membrane can be orderly transported. Rapid vesicular formation and fusion in large numbers are one of the basic traits of all eukaryotic cells.

Cells have complex internal membrane systems. A transporting vesicle obtains its contents from the donor organelle selectively, and fuses with the membrane in a highly selective manner as well. Accordingly, all vesicles must have surface markers which allow the recognition of the target membrane based on their sources and contents, and the target membrane must also have corresponding receptors. Though the mechanism of this recognition remains to be elucidated, a widely noticed theory is that the recognition involves proteins called SNAREs ("SNAP Receptors"). v-SNARE present on the vesicle membrane and t-SNARE present on target membrane have complementary structure and directs vesicular transportation. During the process, a transporting vesicle may examine many possible targets on the membranes before its v-SNARE finds the complementary t-SNARE. According to this theory the recognition is regulated by members of an enzyme family called Rab protein. Rab proteins examine whether the pairing between v-SNARE and t-SNARE is correct. Rab protein binds to the surface of the coated vesicle while the donor membrane is budding to form the vesicles. When the vesicle meets the target membrane, v-SNARE couples with SNARE for a sufficient period of time to allow Rab protein to hydrolyze GTP, and to anchor the vesicle on the target membrane, and subsequent fusion.

The fusion of the inner membranes is catalyzed by a specific fusion protein, which can overcome the inherent energy barrier. Little was known about the mechanism, other than that the process needs ATP, GTP, acyl-coenzyme A and several other proteins, two of which are known: NSF (N-ethylmaleimide-sensitive fusion protein) and SNAPs (soluble NSF attachment proteins). SNAPs shuttle between the fusing membrane and cytoplasma, and bind to v-SNARE on the vesicle membrane and t-SNARE on the target membrane, initiating the assembly of the fusion machinery, which catalyzes the fusion of the lipid bilayers.

SNARE is a family of proteins. The basic functions of SNARE include: (1) it plays a significant regulatory role in the recognition between vesicular and target membranes; and (2) it catalyzes the fusion of lipid bilayers. Besides, because NSF greatly influences the secretory process of platelets and neurotransmitter releases, SNARE, as receptors of NSF, is also important in those processes. (Blood. 1999 94: 1313–8; J. Neurosci. 1998 18: 10241–9). Therefore SNARE plays important roles in the transportation of macromolecules such as proteins, transportation in a cell, the influence of hormone and drugs on cells, metabolism regulation, cell recognition and immunity etc.

The Golgi complex is known to be involved in exocytosis. Some secretory proteins exit the cell through the Golgi complex. The Golgi complex is also a main site of carbohydrate synthesis, where glycoproteins and polysaccharides are synthesized. Aminopolysaccharides are also sulfated in the Golgi complex.

The Golgi complex is also a place for sorting and delivering the products of ER. A large portion of carbohydrates produced in the Golgi complex are attached to proteins and fatty acids from ER as oligosaccharide side chains. Some oligosaccheride groups function as markers and direct proteins to lysosomes or other cellular compartments.

Two types of SNARE have been found in the Golgi complex. Their molecular weight is 28KD and 27KD, respectively, and in humans are located on chromosomes 17q11 and 17q21. They contain a coiled-coil functional domain in the center and an anchoring site on the carboxyl terminal (Science 1996, 272: 1161–3).

In Vitro tests indicate that SNARE protein plays an important role in the recognition and fusion of vesicles and target membrane during the cellular transportation between ER and Golgi complex. (Science 1996, 272: 1161–3; J. Cell Biol. 1996, 133: 507–16)

When a vesicle touches the target membrane, SNARE integrates with soluble SNAP and NSF and forms a 20s complex which promotes membrane fusion. NSF acts as ATPase, probably supplying energy to overcome the energy barrier (Mammalian Genome 7: 850–852, 1996). N-ethylmaleimide-sensitive factor (NSF) is an ATPase which is related to vesicular fusion in eukaryotes. NSF together with SNAP decompose cis-SNARE complex through hydrolyzing ATP, leading to the formation of trans-SNARE complex. Therefore SNARE is important in the forming of proteins in ER-Golgi complex and some relevant transporting processes (Mol Cell 199 Jul. 4(1): 97–107).

Gene mapping data place human GS27 near the gene which causes hereditary hypertension, and there are suggestions that the gene encoding GS27 may be helpful in the diagnoses and treatment of hereditary hypertension (Genomics 1999; 57(2): 285–8).

Through amino acid sequence comparison, the present inventors identified a new human SNARE protein 25 (hSNARE25). It is homologous to SNARE-29KD in rat Golgi complex (database accession # AF035823). hSNARE25 is believed to have some biological functions as SNARE-29KD.

As mentioned above hSNARE25 plays an important role in the regulation of cell division and embryo development. Moreover the regulation process is believed to involve many proteins, so there is a need to identify more proteins involved in these processes, especially to identify their amino acid sequences. The isolation of the gene which codes for SNARE25 protein also forms a foundation for identifying the protein's function, both under healthy and pathologic conditions, and for developing diagnostic and treatment methods.

DESCRIPTION OF THE INVENTION

One objective of the invention is to provide an isolated novel polypeptide, i.e., a Human SNARE protein 25, and fragments, analogues and derivatives thereof.

Another objective of the invention is to provide a polynucleotide encoding said polypeptide.

Another objective of the invention is to provide a recombinant vector containing a polynucleotide encoding a Human SNARE protein 25.

Another objective of the invention is to provide a genetically engineered host cell containing a polynucleotide encoding a Human SNARE protein 25.

Another objective of the invention is to provide a method for producing a Human SNARE protein 25.

Another objective of the invention is to provide an antibody against a Human SNARE protein 25 of the invention.

Another objective of the invention is to provide mimetics, antagonists, agonists, and inhibitors for the polypeptide of the Human SNARE protein 25.

Another objective of the invention is to provide a method for the diagnosis and treatment of the diseases associated with an abnormality of Human SNARE protein 25.

The present invention relates to an isolated polypeptide, which is originated from human, and comprises a polypeptide having the amino acid sequence of SEQ ID NO: 2, or its conservative variants, or its active fragments, or its active derivatives and its analogues. Preferably, the polypeptide has the amino acid sequence of SEQ ID NO: 2.

The present invention also relates to an isolated polynucleotide, comprising a nucleotide sequence or its variant selected from the group consisting of (a) the polynucleotide encoding a polypeptide comprising the amino acid sequence of SEQ ID NO: 2; and (b) a polynucleotide complementary to the polynucleotide (a); (c) a polynucleotide that shares at least 92% homology to the polynucleotide (a) or (b). Preferably, said nucleotide sequence is selected from the group consisting of (a) the sequence of position 6172–846 in SEQ ID NO: 1; and (b) the sequence of position 1–4201 in SEQ ID NO: 1.

The invention also includes: a vector containing a polynucleotide of said invention, especially an expression vector; a host cell genetically engineered with the vector via transformation, transduction or transfection; a method for the production of said inventive polypeptide through the process of host cell cultivation and expression product harvest.

The invention also relates to an antibody which specifically binds to the inventive polypeptide.

The invention also relates to a method for selecting compounds which could simulate, activate, antagonize, or inhibit the activity of the inventive polypeptide and the compounds obtained by the method.

The invention also relates to a method for in vitro diagnosis method of the diseases or disease susceptibility related with the abnormal expression of the inventive polypeptide. The method involves the detection of mutation in the polypeptide or its encoding polynucleotide sequence, or the determination of its quantity and/or biological activity in biological samples.

The invention also relates to pharmaceutical compositions which comprises the inventive polypeptide, its analogues, mimetics, agonists, antagonists, inhibitors, and a pharmaceutically acceptable carrier.

The invention also relates to applications of the inventive polypeptide and/or its polynucleotide for drug development to treat cancers, developmental diseases, immune diseases, or other diseases caused by abnormal expression of the inventive polypeptide.

Other aspects of the invention are apparent to the skilled in the art in view of the disclosure set forth hereinbelow.

The terms used in this specification and claims have the following meanings, unless otherwise noted.

"Nucleotide sequence" refers to oligonucleotide, nucleotide, or polynucleotide and parts of polynucleotide. It also refers to genomic or synthetic DNA or RNA, which could be single stranded or double stranded, and could represent the sense strand or the antisense strand. Similarly, the term "amino acid sequence" refers to oligopeptide, peptide, polypeptide, or protein sequence and parts of proteins. When the "amino acid sequence" in the invention is related to the sequence of a natural protein, the amino acid sequence of said "peptide" or "protein" will not be limited to be identical to the sequence of that natural protein.

"Variant" of a protein or polynucleotide refers to the amino acid sequence or nucleotide sequence, respectively with one or more amino acids or one or more nucleotides changed. Such changes include deletion, insertion, and/or substitution of amino acids in the amino acid sequence, or of nucleotides in the polynucleotide sequence. These changes could be conservative and the substituted amino acid has similar structural or chemical characteristics as the original one, such as the substitution of Ile with Leu. Changes also could be not conservative, such as the substitution of Ala with Trp.

"Deletion" refers to the deletion of one or several amino acids in the amino acid sequence, or of one or several nucleotides in the nucleotide sequence.

"Insertion" or "addition" refers to the addition of one or several amino acids in the amino acid sequence, or of one or several nucleotides in the nucleotide sequence, comparing to the natural molecule. "Substitution" refers to the change of one or several amino acids, or of one or several nucleotides, into different ones without changing number of the residues.

"Biological activity" refers to structural, regulatory or biochemical characteristics of a natural molecule. Similarly, the term "immungenecity" refers to the ability of natural, recombinant, or synthetic proteins to inducing a specific immunological reaction, or of binding specific antibody in appropriate kind of animal or cell.

"Agonist" refers to molecules which regulate, but generally enhance the activity of the inventive polypeptide by binding and changing it. Agonists include proteins, nucleotides, carbohydrates or any other molecules which could bind the inventive polypeptide.

"Antagonist" or "inhibitor" refers to molecules which inhibit or down regulate the biological activity or immunogenecity the inventive polypeptide via binding to it. Antagonists or inhibitors include proteins, nucleotides, carbohydrates or any other molecules which bind to the inventive polypeptide.

"Regulation" refers to changes in function of the inventive polypeptide, including up-regulation or down-regulation of the protein activity, changes in binding specificity, changes of any other biological characteristics, functional or immune characteristics.

"Substantially pure" refers to the condition of substantially free of other naturally related proteins, lipids, saccharides, or other substances. One of ordinary skill in the art can purify the inventive polypeptide by standard protein purification techniques. Substantially pure polypeptide of the invention produces a single main band in a denaturing polyacrylamide gel. The purity of a polypeptide may also be analyzed by amino acid sequence analysis.

"Complementary" or "complementation" refers to the binding of polynucleotides by base pairing under the condition of approximate ion conditions and temperature. For instance, the sequence "C-T-G-A" could bind its complementary sequence "G-A-C-T." The complementation between two single strand molecules could be partial or complete. Homology or sequence similarity between two single strands obviously influences the efficiency and strength of the formed hybrid.

"Homology" refers to the complementary degree, which may be partially or completely homologous. "Partial homology" refers to a sequence being partially complementary to a target nucleotide. The sequence could at least partially inhibit the hybridization between a completely complementary sequence and the target nucleotide. Inhibition of hybridization could be assayed by hybridization (Southern blot or Northern blot) under less stringent conditions. Substantially complementary sequence or hybrid probe could compete with the completely complementary sequence and inhibit its hybridization with the target sequence under less stringent conditions. This doesn't mean that nonspecific binding is allowed under a less stringent condition, because specific or selective reaction is still required.

"Sequence Identity" refers to the percentage of sequence identity or similarity when two or several amino acid or nucleotide sequences are compared. Sequence identity may be determined by computer programs such as MEGALIGN (Lasergene Software Package, DNASTAR, Inc., Madison Wis.). MEGALIGN can compare two or several sequences using different methodologies such as the Cluster method (Higgins, D. G. and P. M. Sharp (1988) Gene 73:237–244). Cluster method examines the distance between all pairs and arrange the sequences into clusters. Then the clusters are partitioned by pair or group. The sequence identity between two amino acid sequences such as sequence A and B can be calculated by the following equation:

$$\frac{\text{Number of paired identical residues between sequences } A \text{ and } B}{\text{Residue number of sequence } A - \text{number of gap residues in sequence } A - \text{number of gap residue in sequence } B} \times 100$$

Sequence identity between nucleotide sequences can also be determined by Cluster method or other well-known methods in the art such as the Jotun Hein method (Hein J., (1990) Methods in Enzymology 183:625–645)

"Similarity" refers to the degree of identity or conservative substitution degree of amino acid residues in corresponding sites of the amino acid sequences when compared to each other. Amino acids for conservative substitution are: negative charged amino acids including Asp and Glu; positive charged amino acids including Leu, Ile and Val; Gly and Ala; Asn and Gln; Ser and Thr; Phe and Tyr.

"Antisense" refers to the nucleotide sequences complementary to a specific DNA or RNA sequence. "Antisense strand" refers to the nucleotide strand complementary to the "sense strand."

"Derivative" refers to the inventive polypeptide or the chemically modified nucleotide encoding it. This kind of modified chemical can be derived from replacement of the hydrogen atom with Alkyl, Acyl, or Amino. The nucleotide derivative can encode peptide retaining the major biological characteristics of the natural molecule.

"Antibody" refers to the intact antibody or its fragments such as Fa, F(ab')2 and Fv, and it can specifically bind to antigenic epitopes of the inventive polypeptide.

"Humanized antibody" refers to an antibody which has its amino acid sequence in non-antigen binding region replaced to mimic human antibody and still retain the original binding activity.

The term "isolated" refers to the removal of a material out of its original environment (for instance, if it's naturally produced, original environment refers to its natural environment). For example, a naturally produced polynucleotide or a polypeptide in its original host organism means it has not been "isolated," while the separation of the polynucleotide or a polypeptide from its coexisting materials in natural system means it was "isolated." This polynucleotide may be a part of a vector, or a part of a compound. Since the vector or compound is not part of its natural environment, the polynucleotide or peptide is still "isolated."

As used herein, the term "isolated" refers to a substance which has been isolated from the original environment. For naturally occurring substance, the original environment is the natural environment. For example, the polynucleotide and polypeptide in a naturally occurring state in the viable cells are not isolated or purified. However, if the same polynucleotide and polypeptide have been isolated from other components naturally accompanying them, they are isolated or purified.

As used herein, "isolated human SNARE protein 25," means that human SNARE protein 25 does not essentially contain other proteins, lipids, carbohydrate or any other substances associated therewith in nature. The skilled in the art can purify human SNARE protein 25, by standard protein purification techniques. The purified polypeptide forms a single main band on a non-reducing PAGE gel. The purity of human SNARE protein 25 can also be analyzed by amino acid sequence analysis.

The invention provides a novel polypeptide—human SNARE protein 25, which comprises the amino acid sequence shown in SEQ ID NO: 2. The polypeptide of the invention may be a recombinant polypeptide, natural polypeptide, or synthetic polypeptide, preferably a recombinant polypeptide. The polypeptide of the invention may be a purified natural product or a chemically synthetic product. Alternatively, it may be produced from prokaryotic or eukaryotic hosts, such as bacterial, yeast, higher plant, insect, and mammal cells, using recombinant techniques. Depending on the host used in the protocol of recombinant production, the polypeptide of the invention may be glycosylated or non-glycosylated. The polypeptide of the invention may or may not comprise the starting Met residue.

The invention further comprises fragments, derivatives and analogues of human SNARE protein 25. As used in the invention, the terms "fragment," "derivative" and "analogue" mean the polypeptide that essentially retains the same biological functions or activity of human SNARE protein 25 of the invention. The fragment, derivative or analogue of the polypeptide of the invention may be (i) one in which one or more of the amino acid residues are substituted with a conserved or non-conserved amino acid residue (preferably a conserved amino acid residue) and such substituted amino acid residue may or may not be one encoded by the genetic code; or (ii) one in which one or more of the amino acid residues are substituted with other residues, including a substituent group; or (iii) one in which the mature polypeptide is fused with another compound, such as a compound to increase the half-life of the polypeptide (for example, polyethylene glycol); or (iv) one in which additional amino acids are fused to the mature polypeptide, such as a leader or secretory sequence or a sequence which is employed for purification of the mature polypeptide or a proprotein sequence. Such fragments, derivatives and analogs are deemed to be within the scope of the skilled in the art from the teachings herein.

The invention provides an isolated nucleic acid or polynucleotide which comprises the polynucleotide encoding an amino acid sequence of SEQ ID NO: 2. The polynucleotide sequence of the invention includes the nucleotide sequence of SEQ ID NO: 1. The polynucleotide of the invention was identified in a human embryonic brain cDNA library. Preferably, it comprises a full-length polynucleotide sequence of 4201 bp, whose ORF (172–846) encodes 224 amino acids. Based on amino acid homology comparison, it is found that the encoded polypeptide is 91% homologous to SNARE-29KD in rat Golgi complex. This novel human SNARE protein 25 has similar structures and biological functions to those of SNARE-29KD in rat Golgi complex.

The polynucleotide according to the invention may be in the forms of DNA or RNA. The forms of DNA include cDNA, genomic DNA, and synthetic DNA, etc., in single stranded or double stranded form. DNA may be an encoding strand or a non-encoding strand. The coding sequence for mature polypeptide may be identical to the coding sequence shown in SEQ ID NO: 1, or is a degenerate sequence. As used herein, the term "degenerate sequence" means a sequence which encodes a protein or peptide comprising a sequence of SEQ ID NO: 2 and which has a nucleotide sequence different from the sequence of coding region in SEQ ID NO: 1.

The polynucleotide encoding the mature polypeptide of SEQ ID NO: 2 includes those encoding only the mature polypeptide, those encoding mature polypeptide plus various additional coding sequence, the coding sequence for mature polypeptide (and optional additional encoding sequence) plus the non-coding sequence.

The term "polynucleotide encoding the polypeptide" includes polynucleotides encoding said polypeptide and polynucleotides comprising additional coding and/or non-coding sequences.

The invention further relates to variants of the above polynucleotides which encode a polypeptide having the same amino acid sequence of invention, or a fragment, analogue and derivative of said polypeptide. The variant of the polynucleotide may be a naturally occurring allelic variant or a non-naturally occurring variant. Such nucleotide variants include substitution, deletion, and insertion variants. As known in the art, an allelic variant may have a substitution, deletion, and insertion of one or more nucleotides without substantially changing the functions of the encoded polypeptide.

The present invention further relates to polynucleotides, which hybridize to the hereinabove-described sequences, that is, there is at least 50% and preferably at least 70% identity between the sequences. The present invention particularly relates to polynucleotides, which hybridize to the polynucleotides of the invention under stringent conditions. As herein used, the term "stringent conditions" means the following conditions: (1) hybridization and washing under low ionic strength and high temperature, such as 0.2×SSC, 0.1% SDS, 60° C.; or (2) hybridization after adding denaturants, such as 50% (v/v) formamide, 0.1% bovine serum/0.1% Ficoll, 42° C.; or (3) hybridization only when the homology of two sequences at least 95%, preferably 97%. Further, the polynucleotides which hybridize to the hereinabove described polynucleotides encode a polypeptide which retains the same biological function and activity as the mature polypeptide of SEQ ID NO: 2

The invention also relates to nucleic acid fragments hybridized with the hereinabove sequence. As used in the present invention, the length of the "nucleic acid fragment" is at least more than 10 bp, preferably at least 20–30 bp, more preferably at least 50–60 bp, and most preferably at least 100 bp. The nucleic acid fragment can be used in amplification techniques of nucleic acid, such as PCR, so as to determine and/or isolate the polynucleotide encoding human SNARE protein 25.

The polypeptide and polynucleotide of the invention are preferably in the isolated form, preferably purified to be homogenous.

According to the invention, the specific nucleic acid sequence encoding human SNARE protein 25 can be obtained in various ways. For example, the polynucleotide is isolated by hybridization techniques well-known in the art, which include, but are not limited to 1) the hybridization between a probe and genomic or cDNA library so as to select a homologous polynucleotid6 sequence, and 2) antibody screening of expression library so as to obtain polynucleotide fragments encoding polypeptides having common structural features.

According to the invention, DNA fragment sequences may further be obtained by the following methods: 1) isolating double-stranded DNA sequence from genomic DNA; and 2) chemical synthesis of DNA sequence so as to obtain the double-stranded DNA.

Among the above methods, the isolation of genomic DNA is least frequently used. A commonly used method is the direct chemical synthesis of DNA sequence. A more frequently used method is the isolation of cDNA sequence. Standard methods for isolating the cDNA of interest is to isolate mRNA from donor cells that highly express said gene followed by reverse transcription of mRNA to form plasmid or phage cDNA library. There are many established techniques for extracting mRNA and the kits are commercially available (e.g. Qiagene). Conventional method can be used to construct cDNA library (Sambrook, et al., Molecular Cloning, A Laboratory Manual, Cold Spring Harbor Laboratory. New York, 1989). The cDNA libraries are also commercially available. For example, Clontech Ltd. has various cDNA libraries. When PCR is further used, even an extremely small amount of expression products can be cloned.

Numerous well-known methods can be used for screening for the polynucleotide of the invention from cDNA library. These methods include, but are not limited to, (1) DNA-DNA or DNA-RNA hybridization; (2) the appearance or loss of the function of the marker-gene; (3) the determination of the level of human SNARE protein 25 transcripts; (4) the determination of protein product of gene expression by immunology methods or the biological activity assays. The above methods can be used alone or in combination.

In method (1), the probe used in the hybridization could be homologous to any portion of polynucleotide of invention. The length of probe is typically at least 10 nucleotides, preferably at least 30 nucleotides, more preferably at least 50 nucleotides, and most preferably at least 100 nucleotides. Furthermore, the length of the probe is usually less than 2000 nucleotides, preferably less than 1000 nucleotides. The probe usually is the DNA sequence chemically synthesized on the basis of the sequence information. Of course, the gene of the invention itself or its fragment can be used as a probe. The labels for DNA probe include, e.g., radioactive isotopes, fluoresceins or enzymes such as alkaline phosphatase.

In method (4), the detection of the protein products expressed by human SNARE protein 25 gene can be carried out by immunology methods, such as Western blotting, radioimmunoassay, and ELISA.

The method of amplification of DNA/RNA by PCR (Saiki, et al. Science 1985; 230:1350–1354) is preferably used to obtain the polynucleotide of the invention. Especially when it is difficult to obtain the full-length cDNA, the method of RACE (RACE—cDNA terminate rapid amplification) is preferably used. The primers used in PCR can be selected according to the polynucleotide sequence information of the invention disclosed herein, and can be synthesized by conventional methods. The amplified DNA/RNA fragments can be isolated and purified by conventional methods such as gel electrophoresis.

Sequencing of polynucleotide sequence of the gene of the invention or its various DNA fragments can be carried out by the conventional dideoxy sequencing method (Sanger et al. PNAS, 1977, 74: 5463–5467). Sequencing of polynucleotide sequence can also be carried out using the commercially available sequencing kits. In order to obtain the full-length cDNA sequence, it is necessary to repeat the sequencing process. Sometimes, it is needed to sequence the cDNA of several clones to obtain the full-length cDNA sequence.

The invention further relates to a vector comprising the polynucleotide of the invention, a genetically engineered host cell transformed with the vector of the invention or directly with the sequence encoding human SNARE protein 25, and a method for producing the polypeptide of the invention by recombinant techniques.

In the present invention, the polynucleotide sequences encoding human SNARE protein 25 may be inserted into a vector to form a recombinant vector containing the polynucleotide of the invention. The term "vector" refers to a bacterial plasmid, bacteriophage, yeast plasmid, plant virus or mammalian virus such as adenovirus, retrovirus or any other vehicle known in the art. Vectors suitable for use in the present invention include, but are not limited to the T7-based expression vector for expression in bacteria (Rosenberg, et al., Gene, 56:125, 1987), the pMSXND expression vector for expression in mammalian cells (Lee and Nathans, J Biol. Chem., 263:3521, 1988) and baculovirus-derived vectors for expression in insect cells. Any plasmid or vector can be used to construct the recombinant expression vector as long as it can replicate and is stable in the host. One important feature of an expression vector is that the expression vector typically contains an origin of replication, a promoter, a marker gene as well as translation regulatory components.

Methods known in the art can be used to construct an expression vector containing the DNA sequence of human SNARE protein 25 and appropriate transcription/translation regulatory components. These methods include in vitro recombinant DNA technique, DNA synthesis technique, in vivo recombinant technique and so on (Sambroook, et al. Molecular Cloning, a Laboratory Manual, cold Spring Harbor Laboratory. New York, 1989). The DNA sequence is operatively linked to a proper promoter in an expression vector to direct the synthesis of mRNA. Exemplary promoters are lac or trp promoter of E. coli; PL promoter of λ phage; eukaryotic promoters including CMV immediate early promoter, HSV thymidine kinase promoter, early and late SV40 promoter, LTRs of retrovirus, and other known promoters which control gene expression in the prokaryotic cells, eukaryotic cells or viruses. The expression vector may further comprise a ribosome binding site for initiating translation, transcription terminator and the like. Transcription in higher eukaryotes is increased by inserting an enhancer sequence into the vector. Enhancers are cis-acting elements of DNA, usually about from 10 to 300 bp in length that act on a promoter to increase gene transcription level. Examples include the SV40 enhancer on the late side of the replication origin 100 to 270 bp, the polyoma enhancer on the late side of the replication origin, and adenovirus enhancers.

Further, the expression vector preferably comprises one or more selective marker genes to provide a phenotype for the selection of the transformed host cells, e.g., the dehydrofolate reductase, neomycin resistance gene and GFP (green flurencent protein) for eukaryotic cells, as well as tetracycline or ampicillin resistance gene for E. coli.

An ordinarily skilled in the art know clearly how to select appropriate vectors, transcriptional regulatory elements, e.g., promoters, enhancers, and selective marker genes.

According to the invention, polynucleotide encoding human SNARE protein 25 or recombinant vector containing said polynucleotide can be transformed or transfected into host cells to construct genetically engineered host cells containing said polynucleotide or said recombinant vector. The term "host cell" means prokaryote, such as bacteria; or primary eukaryote, such as yeast; or higher eukaryotic, such as mammalian cells. Representative examples are bacterial cells, such as E. coli, Streptomyces, Salmonella typhimurium; fungal cells, such as yeast; plant cells; insect cells such as Drosophila S2 or Sf9; animal cells such as CHO, COS or Bowes melanoma.

Transformation of a host cell with the DNA sequence of invention or a recombinant vector containing said DNA sequence may be carried out by conventional techniques as are well known to those skilled in the art. When the host is prokaryotic, such as E. coli, competent cells, which are capable of DNA uptake, can be prepared from cells harvested after exponential growth phase and subsequently treated by the CaCl2 method using procedures well known in the art. Alternatively, MgCl2 can be used. Transformation can also be carried out by electroporation, if desired. When the host is an eukaryote, transfection methods as well as calcium phosphate precipitation may be used. Conventional mechanical procedures such as micro-injection, electroporation, or liposome-mediated transfection may also be used.

The recombinant human SNARE protein 25 can be expressed or produced by the conventional recombinant DNA technology (Science, 1984; 224:1431), using the polynucleotide sequence of the invention. The steps generally include:

(1) transfecting or transforming the appropriate host cells with the polynucleotide (or variant) encoding human SNARE protein 25 of the invention or the recombinant expression vector containing said polynucleotide;

(2) culturing the host cells in an appropriate medium; and (3) isolating or purifying the protein from the medium or cells.

In Step (2) above, depending on the host cells used, the medium for cultivation can be selected from various conventional mediums. The host cells are cultured under a condition suitable for its growth until the host cells grow to an appropriate cell density. Then, the selected promoter is induced by appropriate means (e.g., temperature shift or chemical induction) and cells are cultured for an additional period.

In Step (3), the recombinant polypeptide may be included in the cells, or expressed on the cell membrane, or secreted out of the cell. If desired, physical, chemical and other properties can be utilized in various isolation methods to isolate and purify the recombinant protein. These methods are well-known to those skilled in the art and include, but are not limited to conventional renaturation treatment, treatment by a protein precipitant (such as salt precipitation), centrifugation, cell lysis by osmosis, sonication, supercentrifugation, molecular sieve chromatography or gel chromatography, adsorption chromatography, ion exchange chromatography, HPLC, and any other liquid chromatography, and a combination thereof.

BRIEF DESCRIPTION OF THE DRAWINGS

The following drawings are provided to illustrate the embodiment of the invention, not to limit the scope of invention defined by the claims.

FIG. 1 shows an alignment comparison of amino acid sequences of Human SNARE protein 25 of the invention and SNARE-29KD in rat Golgi complex. The upper sequence is Human SNARE protein 25, and the lower sequence is SNARE-29KD in rat Golgi complex. The identical and similar amino acids are indicated by a one-letter code of amino acid and "+" respectively.

FIG. 2 shows the SDS-PAGE of the isolated Human SNARE protein 25, which has a molecular weight of 25 kDa. The isolated protein band is marked with an arrow.

EXAMPLES

The invention is further illustrated by the following examples. It is appreciated that these examples are only intended to illustrate the invention, not to limit the scope of the invention. For the experimental methods in the following examples, they are performed under routine conditions, e.g., those described by Sambrook. et al., in Molecule Clone: A Laboratory Manual, New York: Cold Spring Harbor Laboratory Press, 1989, or as instructed by the manufacturers, unless otherwise specified.

Example 1
Cloning of Human SNARE Protein 25 Gene

Total RNA from a human embryonic brain was extracted by the one-step method with guanidinium isocyanate/phenol/chloroform. The poly(A) mRNA was isolated from the total RNA with Quik mRNA Isolation Kit (Qiegene). cDNA was prepared by reverse transcription with 2 $\mu$g poly(A) mRNA. The cDNA fragments were inserted into the polyclonal site of pBSK(+) vector (Clontech) using Smart cDNA cloning kit (Clontech) and then transformed into DH5α to form the cDNA library. The 5'- and 3'-ends of all clones were sequenced with Dye terminate cycle reaction sequencing kit (Perkin-Elmer) and ABI 377 Automatic Sequencer (Perkin-Elmer). The sequenced cDNA were compared with the public database of DNA sequences (Genebank) and the DNA sequence of one clone 1007F10 was found to be a novel DNA sequence. The inserted cDNA sequence of clone 1007F10 was dual-directionally sequenced with a serial of synthesized primers. It was indicated that the full length cDNA contained in clone 1007F10 was 4201 bp (SEQ ID NO: 1) with a 675 bp ORF located in positions 172–846 which encoded a novel protein (SEQ ID NO: 2). This clone was named pBS-1007F10 and the encoded protein was named Human SNARE protein 25.

Example 2
Homology Search of cDNA Clone

The homology research of the DNA sequence and its protein sequence of Human SNARE protein 25 of the invention were performed by Blast (Basic local Alignment search tool) (Altschul, S F et al. J. Mol. Biol. 1990; 215: 403–10) in databases such as Genbank, Swissport, etc. The most homologous gene to Human SNARE protein 25 of the invention is known SNARE-29KD in rat Golgi complex. The Genbank accession number of its encoded protein is AF035823. The alignment result of the protein was shown in FIG. 1. Two proteins are highly homologous with an identity of 91% and a similarity of 93%.

Example 3
Cloning Human SNARE Protein 25 Gene by RT-PCR

The template was total RNA extracted from a human embryonic brain. The reverse transcription was carried out with oligo-dT primer to produce cDNAs. After cDNA purified with Qiagen Kit, PCR was carried out with the following primers:

Primer 1: 5'-GGAGATTGCGACGAACAACCAGG-3' (SEQ ID NO: 3)

Primer 2: 5'-CCTTAACAGTTGTTTAATGCAATT-3' (SEQ ID NO: 4)

Primer 1 is the forward sequence started from position 1 of 5' end of SEQ ID NO: 1.

Primer 2 is the reverse sequence of the 3' end of SEQ ID NO: 1.

The amplification condition was a 50 ul reaction system containing 50 mmol/L KCl, 10 mmol/L Tris-Cl (pH8. 5), 1.5 mmol/L MgCl$_2$, 200 umol/L dNTP, 10 pmol of each primer, 1U Taq DNA polymerase(Clontech). The reaction was performed on a PE 9600 DNA amplifier with the following parameters: 94° C. 30 sec, 55° C. 30 sec, and 72° C. 2 min for 25 cycles. β-actin was used as a positive control, and a blank template, as a negative control in RT-PCR. The amplified products were purified with a QIAGEN kit, and linked with a pCR vector (Invitrogen) using a TA Cloning Kit. DNA sequencing results show that the DNA sequence of PCR products was identical to nucleotides 1–4201 bp of SEQ ID NO: 1.

Example 4
Northern Blotting of Expression of Human SNARE Protein 25 Gene

Total RNA was extracted by one-step method (Anal. Biochem 1987, 162, 156–159) with guanidinium isocyanate-phenol-chloroform. That is, homogenate the organize using 4M guanidinium isocyanate-25 mM sodium citrate, 0.2 sodium acetate(pH4.0), add 1 volume phenol and 1/5 volume chloroform-isoamyl alcohol(49:1), centrifuge after mixing. Take out the water phase, add 0.8 volume isopropyl alcohol, then centrifuge the mixture. Wash the RNA precipitation using 70% ethanol, then dry, then dissolve it in the water. 20µg RNA was electrophoresed on the 1.2% agarose gel containing 20 mM 3-(N-morpholino) propane sulfonic acid(pH 7.0)-5 mM sodium acetate-imM EDTA- 2. 2M formaldehyde. Then transfer it to a nitrocellulose filter. Prepare the $^{32}$p-labelled DNA probe with $\alpha$-$^{32}$P dATP by random primer method. The used DNA probe is the coding sequence (172 bp–846 bp) of Human SNARE protein 25 amplified by PCR indicated in FIG. 1. The nitrocellulose filter with the transferred RNA was hybridized with the $^{32}$P-labelled DNA probe (2×10$^6$cpm/ml) overnight in a buffer containing 50% formamide-25 mM KH$_2$PO$_4$(Ph7.4)- 5× Denhardt's solution and 200 µg /ml salmine. Then wash the filter in the 1×SSC-0.1% SDS, at 55° C., for 30 min. Then analyze and quantitative determinate using Phosphor Imager.

Example 5
In vitro Expression, Isolation and Purification of Recombinant Human SNARE Protein 25

A pair of primers for specific amplification was designed based on SEQ ID NO: 1 and the encoding region in FIG. 1, the sequences are as follows:
Primer3:
5'-CCCCATATGATGTGTCGTCCGACTTCGAAGGTTACG-3' (SEQ ID NO: 5)
Primer4:
5'-CCCGTCGACTCAGTGTCTTCTGACAGAAAAAGTG-3' (SEQ ID NO: 6)

These two primers contain a NdeI and SalI cleavage site on the 5' end respectively. Within the sites are the coding sequences of the 5' and 3' end of the desired gene. NdeI and SalI cleavage sites were corresponding to the selective cleavage sites on the expression vector pET-28b(+) (Novagen, Cat. No. 69865.3). PCR amplification was performed with the plasmid pBS-1007F10 containing the full-length target gene as a template. The PCR reaction was subject to a 50 µl system containing 10 pg pBS-1007F10plasmid, 10 pmol of Primer-3 and 10 pmol of Primer-4, 1 µl of Advantage polymerase Mix (Clontech). The parameters of PCR were 94° C. 20 sec, 60° C. 30 sec, and 68° C. 2 min for 25 cycles. After digesting the amplification products and the plasmid pET-28(+) by NdeI and SalI, the large fragments were recovered and ligated with T4 ligase. The ligated product was transformed into *E. coli* DH5α with the calcium chloride method. After cultured overnight on a LB plate containing a final concentration of 30 µg/ml kanamycin, positive clones were selected out using colony PCR and then sequenced. The positive clone (pET-1007F10) with the correct sequence was selected out and the recombinant plasmid thereof was transformed into BL21 (DE3)plySs (Novagen) using the calcium chloride method. In a LB liquid medium containing a final concentration of 30 µg/ml of kanamycin, the host bacteria BL21(pET-1007F10) were cultured at 37° C. to the exponential growth phase, then IPTG were added with the final concentration of 1 mmol/L, the cells were cultured for another 5 hours, and then centrifuged to harvest the bacteria. After the bacteria were sonicated, the supernatant was collected by centrifugation. Then the purified desired protein—Human SNARE protein 25 was obtained by a His. Bind Quick Cartridge (Novagen) affinity column with binding 6His-Tag. SDS-PAGE showed a single band at 25 kDa (FIG. 2). The band was transferred onto the PVDF membrane and the N terminal amino acid was sequenced by Edams Hydrolysis, which shows that the first 15 amino acids on N-terminus were identical to those in SEQ ID NO: 2.

Example 6
Preparation of Antibody Against Human SNARE Protein 25

The following specific Human SNARE protein 25 polypeptide was synthesized by a polypeptide synthesizer (PE-ABI): NH2-Met-Ser-Ser-Asp-Phe-Glu-Gly-Tyr-Glu-Gln-Asp-Phe-Ala-Val-Leu-COOH (SEQ ID NO: 7). The polypeptide was conjugated with hemocyanin and bovine serum albumin (BSA) respectively to form two composites (See Avrameas et al., Immunochemistry, 1969, 6:43). 4 mg of hemocyanin-polypeptide composite was used to immunize rabbit together with Freund's complete adjuvant. The rabbit was re-immunized with the hemocyanin-polypeptide composite and Freund's incomplete adjuvent 15 days later. The titer of antibody in the rabbit sera was determined with a titration plate coated with 15 µg/ml BSA-polypeptide composite by ELISA. The total IgG was isolated from the sera of an antibody positive rabbit with Protein A-Sepharose. The polypeptide was bound to Sepharose 4B column activated by cyanogen bromide. The antibodies against the polypeptide were isolated from the total IgG by affinity chromatography. The immunoprecipitation approved that the purified antibodies could specifically bind to Human SNARE protein 25.

INDUSTRIAL APPLICABILITY

The polypeptide of the invention and antagonists, agonists and inhibitors thereof can be directly used for the treatment of diseases, e.g., various malignant tumors or cancers, dermatitis, inflammation, HIV infection and immune system diseases.

The polypeptide of this invention, human SNARE protein 25, is a SNAP (soluble NSF-binding protein) receptor protein. Its functions in cells include: (1) specific recognition between vesicle and target-membrane; and (2) catalyzing the fusion of lipid bi-layers. Moreover, the polypeptide of the invention has a significant effect on the processes of secretion of platelet granules, release of neurotransmitter and so on. So as the receptor of NSF binding-protein, SNARE is an important protein in the above processes.

The polypeptide of the invention (Human SNARE protein 25) is of great significance in the processes of secretion of macro-molecules (e.g. protein), cellular transportation, effects of hormones and other drug molecules on cells, metabolism regulation, cellular recognition, and immunization, etc.

The polypeptide of the invention (human SNARE protein 25) can be used to diagnose and treat many diseases, including but not limited: various malignant tumors, endocrine system diseases, diseases related to growth and development, nervous system diseases, immune diseases, acquired immune deficiency symptoms (AIDS).

The polypeptide also can be used to treat common human nervous system diseases, including:

(1) Brain Diseases: cerebrovascular diseases: transient cerebral ischemia, cerebral embolism, encephalorrhagia, subarachnoid hemorrhage; Intracranial space-occupying lesion: neuroglioma, meningioma, neurofibroma, pituitary adenoma, and encephalic granuloma.

Neurodegenerative Diseases: Alzheimer's Disease, Parkinson's Disease, chorea, depression, amnesia, Huntington's disease, epilepsy, migraine, dementia, multiple sclerosis.

(2) Neuromuscular Diseases: myasthenia gravis, spinal muscle atrophy, muscle pseudohypertrophy, Duchenne muscle cacotrophia, tetanic muscle cacotrophia, muscle catatonia tardive dyskinesia, muscle tension handicap.

(3) Neurocataneous Syndrome: fibroneuroma, tubercular sclerosis, cerebral trigeminal angioma, ataxia-telangiectasia.

(4) Mental Diseases: schizophrenia, depression, paranoia, anxiety, compulsion, fearing, and neurasthenia.

(5) Spinal Cord Diseases: acute myelitis, spinal cord compression (6) Peripheral Nervous Diseases: prosopalgia, facial palsy, bulbar palsy, sciatica, and Guillain-Barre Syndrome.

The polypeptide of the invention may also be used to treat developmental disorders, including: bifid spine, cranioschisis, anencephaly, craniocele, schizencephalic porencephaly, Down's syndrome, congenital encephaledema, aqueduct cacogenesis, achondroplastic dwarf, hypogenesis of spinal skeleton, pseudocartilage hypoplasia, Langer-Giedion syndrome, funnel chest, hypogenitalism, congenital adrenal cortical hyperplasia, epispadias, enorchia, cacogenesis syndrome associated with microsoma (e.g. Conradi syndrome and Danbolt-closs syndrome), congenital cataract, congenital phacometachoresis; congenital microblepharia, retina dysplasia, congenital optic atrophy, congenital sensory nerve hearing loss, acrorhagadia, teratism, williams syndrome, Alagille syndrome, Bechwith-Widedemann syndrome and so on.

Human SNARE protein 25 may also be used to treat various tumors, such as: tumors of epithelial tissues (e.g. basal lamina epithelial, imbrication epithelial, mucus cell etc.), connective tissues (e.g. Fiber tissue, adipose tissue, cartilage tissue, smooth muscle tissue, blood vessel and lymphangioencothelium tissue, etc.), hemopoietic tissues (e.g. B cell, T cell, tissue cell, etc), central nervous tissues, peripheral nervous tissues, endorcrine tissues, sexual gland tissues, special tissues (e.g. tooth tissue). For example: gastric cancinoma, hepatoma, large intestines cancer, galactophore cancer, lung cancer, prostate cancer, cancer of uterine cervix, pancreatic cancer, oesophagus cancer, etc.

The polypeptide of the invention (human SNARE protein 25) also is an immunomodulator, functioning either as an immuno-depressor or immuno-stimulant. It can be used to treat abnormal immunoreaction, anergy and immune tolerance, and host-defense failure. The polypeptide and its antibody may also be effective in treating diseases caused by demages to the immune system, immune deficiency or disorders, such as hemopoietic system diseases (e.g. pernicious anemia), dermatitis (e.g. psoriasis), autoimmune diseases (e.g. rheumatoid arthritis), radioactive diseases and the formation and regulation lymphocytes.

The polypeptide (human SNARE protein 25) are used for treating inflammation reactions, such as: allergic reaction, bronchial asthma, allergic pneumonia, adult respiratory distress, lung eosinopenia, sarcoidosis, rheumatic arthritis, rheumatoid arthritis, osteoarthritis, cholecystitis, glomerulonephritis, immune complex-mediated glomerulonephritis, acute uveitis, osteoporosis, dermatomyositis, hives, specific dermatitis, hemochromatiosis, polymysitis, Addision disease, Greffis disease, chronic active hepatitis, Green-Barry syndrome, encephalic granuloma, Wegener granuloma, autoimmune thyroiditis, autoimmune interstitial nephritis, ulcerative colitis, hemophthisis, panctratitits, segmental ileitis, myocarditis, atherosclerosis atherosis, multiple scleroderma, inflammation caused by infection and injury and so on.

The invention also provides methods for screening compounds so as to identify an agent which enhances Human SNARE protein 25 activity (agonists) or decrease Human SNARE protein 25 activity (antagonists). The agonists enhance the biological functions of Human SNARE protein 25 such as inactivation of cell proliferation, while the antagonists prevent and alleviate the disorders associated with the excess cell proliferation, such as various cancers. For example, in the presence of an agent, the mammal cells or the membrane preparation expressing Human SNARE protein 25 can be incubated with the labeled Human SNARE protein 25 to determine the ability of the agent to enhance or repress the interaction.

Antagonists of Human SNARE protein 25 include antibodies, compounds, receptor deletants and analogues. The antagonists of Human SNARE protein 25 can bind to Human SNARE protein 25 and eliminate or reduce its function, or inhibit the production of Human SNARE protein 25, or bind to the active site of said polypeptide so that the polypeptide can not function biologically.

When screening for compounds as an antagonist, Human SNARE protein 25 may be added into a biological assay. It can be determined whether the compound is an antagonist or not by determining its effect on the interaction between Human SNARE protein 25 and its receptor. Using the same method as that for screening compounds, receptor deletants and analogues acting as antagonists can be selected. Polypeptide molecules capable of binding to Human SNARE protein 25 can be obtained by screening a polypeptide library comprising various combinations of amino acids bound onto a solid matrix. Usually, Human SNARE protein 25 is labeled in the screening.

The invention further provides a method for producing antibodies using the polypeptide, and its fragment, derivative, analogue or cells as an antigen. These antibodies may be polyclonal or monoclonal antibodies. The invention also provides antibodies against epitopes of Human SNARE protein 25. These antibodies include, but are not limited to, polyclonal antibody, monoclonal antibody, chimeric antibody, single-chain antibody, Fab fragment and the fragments produced by a Fab expression library.

Polyclonal antibodies can be prepared by immunizing animals, such as rabbit, mouse, and rat, with Human SNARE protein 25. Various adjuvants, including but are not limited to Freund's adjuvant, can be used to enhance the immunization. The techniques for producing Human SNARE protein 25 monoclonal antibodies include, but are not limited to, the hybridoma technique (Kohler and Milstein. Nature, 1975, 256: 495–497), the trioma technique, the human B-cell hybridoma technique, the EBV-hybridoma technique and so on. A chimeric antibody comprising a constant region of human origin and a variable region of non-human origin can be produced using methods well-known in the art (Morrison et al, PNAS, 1985, 81: 6851). Furthermore, techniques for producing a single-chain antibody (U.S. Pat. No. 4,946,778) are also useful for preparing single-chain antibodies against Human SNARE protein 25.

The antibody against Human SNARE protein 25 can be used in immunohistochemical method to detect the presence of Human SNARE protein 25 in a biopsy specimen.

The monoclonal antibody specific to Human SNARE protein 25 can be labeled by radioactive isotopes, and injected into human body to trace the location and distribution of Human SNARE protein 25. This radioactively labeled antibody can be used in the non-wounding diagnostic method for the determination of tumor location and metastasis.

Antibodies can also be designed as an immunotoxin targeting a particular site in the body. For example, a monoclonal antibody having high affinity to Human SNARE protein 25 can be covalently bound to bacterial or plant toxins, such as diphtheria toxin, ricin, ormosine. One common method is to challenge the amino group on the antibody with sulfydryl cross-linking agents, such as SPDP, and bind the toxin onto the antibody by interchanging the disulfide bonds. This hybrid antibody can be used to kill Human SNARE protein 25-positive cells.

The antibody of the invention is useful for the therapy or the prophylaxis of disorders related to the Human SNARE protein 25. The appropriate amount of antibody can be administrated to stimulate or block the production or activity of Human SNARE protein 25.

The invention further provides diagnostic assays for quantitative and in situ measurement of Human SNARE protein 25 level. These assays are well known in the art and include FISH assay and radioimmunoassay. The level of Human SNARE protein 25 detected in the assay can be used to illustrate the importance of Human SNARE protein 25 in diseases and to determine the diseases associated with Human SNARE protein 25.

The polypeptide of the invention is useful in the analysis of polypeptide profile. For example, the polypeptide can be specifically digested by physical, chemical, or enzymatic means, and then analyzed by one, two or three dimensional gel electrophoresis, preferably by spectrometry.

New Human SNARE protein 25 polynucleotides also have many therapeutic applications. Gene therapy technology can be used in the therapy of abnormal cell proliferation, development or metabolism, which are caused by the loss of Human SNARE protein 25 expression or the abnormal or non-active expression of Human SNARE protein 25. Recombinant gene therapy vectors, such as virus vectors, can be designed to express mutated Human SNARE protein 25 so as to inhibit the activity of endogenous Human SNARE protein 25. For example, one form of mutated Human SNARE protein 25 is a truncated Human SNARE protein 25 whose signal transduction domain is deleted. Therefore, this mutated Human SNARE protein 25 can bind the downstream substrate without the activity of signal transduction. Thus, the recombinant gene therapy vectors can be used to treat diseases caused by abnormal expression or activity of Human SNARE protein 25. The expression vectors derived from a virus, such as retrovirus, adenovirus, adeno-associated virus, herpes simplex virus, parvovirus, and so on, can be used to introduce the Human SNARE protein 25 gene into the cells. The methods for constructing a recombinant virus vector harboring Human SNARE protein 25 gene are described in the literature (Sambrook, et al. supra). In addition, the recombinant Human SNARE protein 25 gene can be packed into liposome and then transferred into the cells.

The methods for introducing the polynucleotides into tissues or cells include directly injecting the polynucleotides into tissue in the body; or introducing the polynucleotides into cells in vitro with vectors, such as virus, phage, or plasmid, etc, and then transplanting the cells into the body.

Also included in the invention are ribozyme and the oligonucleotides, including antisense RNA and DNA, which inhibit the translation of the Human SNARE protein 25 mRNA. Ribozyme is an enzyme-like RNA molecule capable of specifically cutting certain RNA. The mechanism is nucleic acid endo-cleavage following specific hybridization of ribozyme molecule and the complementary target RNA. Antisense RNA and DNA as well as ribozyme can be prepared by using any conventional techniques for RNA and DNA synthesis, e.g., the widely used solid phase phosphite chemical method for oligonucleotide synthesis. Antisense RNA molecule can be obtained by the in vivo or in vitro transcription of the DNA sequence encoding said RNA, wherein said DNA sequence is integrated into the vector and downstream of the RNA polymerase promoter. In order to increase its stability, a nucleic acid molecule can be modified in many manners, e.g., increasing the length of two the flanking sequences, replacing the phosphodiester bond with the phosphothioester bond in the oligonucleotide.

The polynucleotide encoding Human SNARE protein 25 can be used in the diagnosis of Human SNARE protein 25 related diseases. The polynucleotide encoding Human SNARE protein 25 can be used to detect whether Human SNARE protein 25 is expressed or not, and whether the expression of Human SNARE protein 25 is normal or abnormal in the case of diseases. For example, Human SNARE protein 25 DNA sequences can be used in the hybridization with biopsy samples to determine the expression of Human SNARE protein 25. The hybridization methods include Southern blotting, Northern blotting and in situ blotting, etc., which are well-known and established techniques. The corresponding kits are commercially available. A part of or all of the polynucleotides of the invention can be used as probe and fixed on a microarray or DNA chip for analysis of differential expression of genes in tissues and for the diagnosis of genes. The Human SNARE protein 25 specific primers can be used in RNA-polymerase chain reaction and in vitro amplification to detect transcripts of Human SNARE protein 25.

Further, detection of mutations in Human SNARE protein 25 gene is useful for the diagnosis of Human SNARE protein 25-related diseases. Mutations of Human SNARE protein 25 include site mutation, translocation, deletion, rearrangement and any other mutations compared with the wild-type Human SNARE protein 25 DNA sequence. The conventional methods, such as Southern blotting, DNA sequencing, PCR and in situ blotting, can be used to detect a mutation. Moreover, mutations sometimes affects the expression of protein. Therefore, Northern blotting and Western blotting can be used to indirectly determine whether the gene is mutated or not.

Sequences of the present invention are also valuable for chromosome identification. The sequence is specifically targeted to and can hybridize with a particular location on an individual human chromosome. There is a current need for identifying particular sites of gene on the chromosome. Few chromosome marking reagents based on actual sequence data (repeat polymorphism) are presently available for marking chromosomal location. The mapping of DNA to chromosomes according to the present invention is an important first step in correlating those sequences with genes associated with disease.

Briefly, sequences can be mapped to chromosomes by preparing PCR primers (preferably 15–35 bp) from the cDNA. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the oligonucleotide primers of the invention, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clones to a metaphase chromosomal spread can be used to provide a precise chromosomal location in one step. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis.

Next, it is necessary to determine the differences in the cDNA or genomic sequence between affected and unaffected individuals. If a mutation is observed in some or all of the affected individuals but not in any normal individuals, then the mutation is likely to be the cause of the disease. Comparison of affected and unaffected individuals generally involves first looking for structural alterations in the chromosomes, such as deletions or translocations, that are visible from chromosome level, or detectable using PCR based on that DNA sequence. With current resolution of physical mapping and genetic mapping techniques, a cDNA precisely localized to a chromosomal region associated with the disease could be one of 50 to 500 potential causative genes. (This assumes 1 megabase mapping resolution and one gene per 20 kb).

According to the invention, the polypeptides, polynucleotides and its mimetics, agonists, antagonists and inhibitors may be employed in combination with a suitable pharmaceutical carrier. Such a carrier includes but is not limited to water, glucose, ethanol, salt, buffer, glycerol, and combinations thereof. Such compositions comprise a safe and effective amount of the polypeptide or antagonist, as well as a pharmaceutically acceptable carrier or excipient with no influence on the effect of the drug. These compositions can be used as drugs in disease treatment.

The invention also provides a pharmaceutical pack or kit comprising one or more containers filled with one or more of the ingredients of the pharmaceutical compositions of the invention. With such container(s) there may be a notice from a governmental agency, that regulates the manufacture, use or sale of pharmaceuticals or biological products, the notice reflects government's approval for the manufacture, use or sale for human administration. In addition, the polypeptides of the invention may be employed in conjunction with other therapeutic compounds.

The pharmaceutical compositions may be administered in a convenient manner, such as through topical, intravenous, intraperitoneal, intramuscular, subcutaneous, intranasal or intradermal routes. Human SNARE protein 25 is administered in an amount, which is effective for treating and/or prophylaxis of the specific indication. The amount of Human SNARE protein 25 administrated on patient will depend upon various factors, such as delivery methods, the subject health, judgment of the skilled clinician.

We claim:

1. An isolated polypeptide having a human SNARE protein 25 activity and comprising an amino acid sequence of SEQ ID NO: 2.

2. An isolated polypeptide having a human SNARE protein 25 activity and comprising an amino acid sequence that is at least 97% identical to SEQ ID NO: 2.

3. A pharmaceutical composition comprising a polypeptide according to claim 2, and a pharmaceutically acceptable carrier.

* * * * *

SEQUENCE LISTING

```
<160> NUMBER OF SEQ ID NOS: 7

<210> SEQ ID NO 1
<211> LENGTH: 4201
<212> TYPE: DNA
<213> ORGANISM: Homo sapiens
<220> FEATURE:
<221> NAME/KEY: CDS
<222> LOCATION: (172)..(846)
<223> OTHER INFORMATION:

<400> SEQUENCE: 1
ggagattgcg acgaacaacc aggaagcggc tgggttgaga gctgtccccg gttctccgtt      60
ctgctctcgg gggcaccttc cggggttcct aagccgcggg gcccctcgct gcccctcgag     120
gcccttcccc tgacctaggc tttggcctgg gctactcgtt ccggagccgc c atg tcg     177
                                                          Met Ser
                                                            1 tcc gac ttc gaa ggt tac gag cag gac ttc gcg gtg ctc act gca gag     225
Ser Asp Phe Glu Gly Tyr Glu Gln Asp Phe Ala Val Leu Thr Ala Glu
      5                  10                  15 atc acc agc aag att gcg agg gtc cca cga ctc ccg cct gat gaa aag     273
Ile Thr Ser Lys Ile Ala Arg Val Pro Arg Leu Pro Pro Asp Glu Lys
   20                  25                  30 aaa cag atg gtt gca aat gtg gag aaa cag ctt gaa gaa gcg aaa gaa     321
```

```
Lys Gln Met Val Ala Asn Val Glu Lys Gln Leu Glu Ala Lys Glu
 35                  40                  45                  50 ctg ctt gaa cag atg gat ttg gaa gtc cga gag ata cca ccc caa agt       369
Leu Leu Glu Gln Met Asp Leu Glu Val Arg Glu Ile Pro Pro Gln Ser
                     55                  60                  65 cga ggg atg tac agc aac aga atg aga agc tac aaa caa gaa atg gga       417
Arg Gly Met Tyr Ser Asn Arg Met Arg Ser Tyr Lys Gln Glu Met Gly
                 70                  75                  80 aaa ctc gaa aca gat ttt aaa agg tca cgg atc gcc tac agt gac gaa       465
Lys Leu Glu Thr Asp Phe Lys Arg Ser Arg Ile Ala Tyr Ser Asp Glu
             85                  90                  95 gta cgg aat gag ctc ctg ggg gat gat ggg aat tcc tca gag aac cag       513
Val Arg Asn Glu Leu Leu Gly Asp Asp Gly Asn Ser Ser Glu Asn Gln
        100                 105                 110 ttg ata aaa tta cgt gaa gag agg gca cat ctg ctc gat aac aca gag       561
Leu Ile Lys Leu Arg Glu Glu Arg Ala His Leu Leu Asp Asn Thr Glu
115                 120                 125                 130 agg ctg gaa agg tca tct cgg aga cta gag gct gga tac caa ata gca       609
Arg Leu Glu Arg Ser Ser Arg Arg Leu Glu Ala Gly Tyr Gln Ile Ala
                135                 140                 145 gtg gaa acc gag caa att ggt cag gag atg ttg gaa aac ctt agt cat       657
Val Glu Thr Glu Gln Ile Gly Gln Glu Met Leu Glu Asn Leu Ser His
            150                 155                 160 gac aga gaa aag ata cag cga gca cgt gaa aga ctt cgg gaa aca gat       705
Asp Arg Glu Lys Ile Gln Arg Ala Arg Glu Arg Leu Arg Glu Thr Asp
        165                 170                 175 gct aat ttg gga aaa agc tcc agg att ctg aca ggg atg ttg cga aga       753
Ala Asn Leu Gly Lys Ser Ser Arg Ile Leu Thr Gly Met Leu Arg Arg
    180                 185                 190 atc atc cag aac cgc atc ctg ctc gtc atc cta ggg atc atc gtg gtc       801
Ile Ile Gln Asn Arg Ile Leu Leu Val Ile Leu Gly Ile Ile Val Val
195                 200                 205                 210 atc acc atc ctg atg gcg atc act ttt tct gtc aga aga cac tga           846
Ile Thr Ile Leu Met Ala Ile Thr Phe Ser Val Arg Arg His
                215                 220 tgtatctgct ctcccttgat aaacagcaac aacagcttgt tctgagtaat taagacaaaa     906
tggtcacatg aatcattctg ttgcgctgac aggccccagg tgaccctctc tctccctcac     966
cgccgttggg ctgaagtgca aagagtgtaa aaatatttc  tattcctgtt tgcatgtggg    1026
ttggtttcct tttcgaggtt tgtcttcacc cagattcgtt ttttagaggg gaaggtgaat    1086
gtttatttac cttttttgcta atgtcatcaa ctagccaaaa tagccccagt gacactccta    1146
gccctctgga cgtgtcaagg gccgtggttt gggagaggac atgatgagtc agtcacgaga    1206
gcttctgttt gtcacccgcc tcttgttgct gaaaagctct tctgtgatgt ctgaggataa    1266
aaatgcagca aaaagcaggg gatggagtca gtgaccccgt ccagcaagcc agccctgttc    1326
ctacacaggc tcatgaata  tagtcatcaa cctgcctgag tgctttcatt gtaaaggtcg    1386
gtatttaatg tcggttgtac aggaaattga cttagcactt tccctgtttt tctattgcat    1446
aatttttttt ttaacccaaa gatattttt  ttgctgagcc tgcccagtat tcactgttca    1506
caactttgat tactggctac aagaaatatt ttcttgcctt ccccaaatcc catactcccc    1566
agaatctgct ggcaaagtga gccctggtac aggatttaat tgtgacctcg tcttccctga    1626
cctgtgtaag catctctgta tcctttcggt tttaatatct gcactgccaa aagcagtcct    1686
catacttgca aaaggtctga caaggttctc tccacataca ttccagtatg taaagagacc    1746
atgaatattt cagtaagagc aagaacatga ctccatcagt gtgaaatttc aaatgtgatt    1806
```

```
ataaatatgg gagagtccta taggagggtc caccagagat aaacttcacg gaaaacgttc  1866
cctaacctcc tttaaaagaa tagaggatgg cagattgttc caaaaggaat ggcttgggtt  1926
tttaactaac aaatgttagc aagcctttct tgaattcact atgtattcaa acttctaata  1986
tgctttgtga ttttttttctt tcatttcttt ctgtctgagg taaccaggaa ttgcgttcaa  2046
aatgagctca tttgtgatca ggcttaaaag ttgcccaagc tgaggtcgtt tcccccagt   2106 cacaaagcag aatgttttc tcaagacttc ataggcactt actggtccgt actatctttg   2166
gaatataatt agaagctttg aatccttgaa aagcaaacct gttctcttca tcaaaaatgc  2226
taaccacctg tgcccgtgga tcaatatcac ctggatgtag tgcttgatat ttttcccaac  2286
tcagaagaaa accattatgg tttagagagg aaatgcagaa tggcagaatc caccagagaa  2346
attgcactta tcgaaacagg ccaaggcctg catgtgttcg ataaatcat ttagtattgt    2406 gtaaataaag ctgcagcctt tacttcggag ggatggtgtg ggattttggc tgagggaagc  2466
aggacagaga aggagcagga agctatgcta attttcctgt cagcttaagg gatccgtctc  2526
agcaagaatc ttgtattctg ataacggaat gctgtacgtg ctgaccacat ctaagaacca  2586
ttaaaaagca aggaaacaaa caaacaaccc ttttctcatt ccgacacacg aatagtcatc  2646
gagtattaca ccagcccctc tggtggcttc cttcaaaact gttgatctta gctaaagtgt  2706
ataaccagtt accagctgca cttcgcacgg ccatcccgtc cacaatgcag cagactcttc  2766
ccaaggccac ctagcaagca aggttgatcg gatcatctaa actggccgcc tcctgaatat  2826
ttcactgaat cctggcgttc atgttgaagc agacaaaatg agaaggagg agggcattgc   2886 tcacctctca atagcttttt tcgttcaagt tctatgtctt tatcagctct tgcctgtgat  2946
tttaccccaa ttcaaccttg ggagtgggaa gaatatgaac agataaccct tggcctaaca  3006
gctccatcaa acctccttga gagcaactac ctaggccagg ctagtgagtg ctttgtgagg  3066
aagctggtca gaaggttccc tcaactcctt cctggtcctc ctggacactg cagaaaagac  3126 ttagggatc cccagcagag gccaattgct ctccttcctt ccctgcccca ccaggaaagg   3186
aataacgtcc acagacttga agcagatagt gaagtagatc tgtgagaggt tctaggtact  3246
tagtgtgtag actttgacga atatttctca agttgggagc ccttgttaaa aatgatgttt  3306
aagggagtgg ttgggggggaa gatgaaggca tggaggagga agaagagaag gaagcccttg  3366
ccatataaaa ttcatgcaga ctaaacagtt tccctgacag aataaataaa gtggatgcta  3426
ccccactcca gaatcaaaag caatttaatt aaagtctctt aagttgtaaa gagttttaaa  3486
tgatccgtgt tgaaggcgaa tgcctgcaaa tgcagtgggc tgacgtcag ctgccgggcc    3546 tgggctggga ggccatttgc tattctgttt aaggcaggct ggattgtctt attttggaac  3606
cagcttggtg gggggtttgc tttgctactg cttctgagcc ctgagcttca aaggctgaaa  3666
ttaatggtga acaaaattgt gcggctctgg ccatcccatg cggggcaagc ccattgaggg  3726
ttatcattaa gtaaagaaat aaagaggggg aaaaaagcct gcctgttcca aaaacctcat  3786
cagataatga cctcagtgat tgggttttca ttaccaaaca gcatccagag attatcaacc  3846
catagaagaa gggagggaa aaaagaaag aaaggaaaag caactgtctt tctctccctc     3906
tctttctcct ttttttttgc acatctttc tttaaaactg tcagatcatt tcagtatttc    3966
aaatccgagg aaaacagcct gcctgctgct gtatttgaag ttgtaatggt gtcaaaaagt  4026
cacgactgac tgacagccgt cagtcccaga ggggctcatt aaatcataaa aacttgacaa  4086
ggaaataatt gcgcattgcc agcaacttgg cgcctgttta gacgttttta ttttctttca  4146
ttattagtcc ccaccattac gttcattaac aaattgcatt aaacaactgt taagg         4201
```

<210> SEQ ID NO 2
<211> LENGTH: 224
<212> TYPE: PRT
<213> ORGANISM: Homo sapiens

<400> SEQUENCE: 2

```
Met Ser Ser Asp Phe Glu Gly Tyr Glu Gln Asp Phe Ala Val Leu Thr
  1               5                  10                  15
Ala Glu Ile Thr Ser Lys Ile Ala Arg Val Pro Arg Leu Pro Pro Asp
             20                  25                  30
Glu Lys Lys Gln Met Val Ala Asn Val Glu Lys Gln Leu Glu Glu Ala
         35                  40                  45
Lys Glu Leu Leu Glu Gln Met Asp Leu Glu Val Arg Glu Ile Pro Pro
 50                  55                  60
Gln Ser Arg Gly Met Tyr Ser Asn Arg Met Arg Ser Tyr Lys Gln Glu
 65                  70                  75                  80
Met Gly Lys Leu Glu Thr Asp Phe Lys Arg Ser Arg Ile Ala Tyr Ser
                 85                  90                  95
Asp Glu Val Arg Asn Glu Leu Leu Gly Asp Asp Gly Asn Ser Ser Glu
            100                 105                 110
Asn Gln Leu Ile Lys Leu Arg Glu Glu Arg Ala His Leu Leu Asp Asn
        115                 120                 125
Thr Glu Arg Leu Glu Arg Ser Ser Arg Arg Leu Glu Ala Gly Tyr Gln
130                 135                 140
Ile Ala Val Glu Thr Glu Gln Ile Gly Gln Glu Met Leu Glu Asn Leu
145                 150                 155                 160
Ser His Asp Arg Glu Lys Ile Gln Arg Ala Arg Glu Arg Leu Arg Glu
                165                 170                 175
Thr Asp Ala Asn Leu Gly Lys Ser Ser Arg Ile Leu Thr Gly Met Leu
            180                 185                 190
Arg Arg Ile Ile Gln Asn Arg Ile Leu Leu Val Ile Leu Gly Ile Ile
        195                 200                 205
Val Val Ile Thr Ile Leu Met Ala Ile Thr Phe Ser Val Arg Arg His
210                 215                 220
```

<210> SEQ ID NO 3
<211> LENGTH: 23
<212> TYPE: DNA
<213> ORGANISM: Artificial
<220> FEATURE:
<223> OTHER INFORMATION: (oligonucleotide primer)

<400> SEQUENCE: 3
ggagattgcg acgaacaacc agg                                          23

<210> SEQ ID NO 4
<211> LENGTH: 24
<212> TYPE: DNA
<213> ORGANISM: Artificial
<220> FEATURE:
<223> OTHER INFORMATION: (oligonucleotide primer)

<400> SEQUENCE: 4
ccttaacagt tgtttaatgc aatt                                         24

<210> SEQ ID NO 5
<211> LENGTH: 32
<212> TYPE: DNA

```
<213> ORGANISM: Artificial
<220> FEATURE:
<223> OTHER INFORMATION: (oligonucleotide primer)

<400> SEQUENCE: 5
cagccatggc ggggaagaag aatgttctgt cg                                      32

<210> SEQ ID NO 6
<211> LENGTH: 29
<212> TYPE: DNA
<213> ORGANISM: Artificial
<220> FEATURE:
<223> OTHER INFORMATION: (oligonucleotide primer)

<400> SEQUENCE: 6
cccggatccc gctgcttggc cttcttcac                                          29

<210> SEQ ID NO 7
<211> LENGTH: 15
<212> TYPE: PRT
<213> ORGANISM: Artificial
<220> FEATURE:
<223> OTHER INFORMATION: (partial sequence of SEQ ID NO.: 2)

<400> SEQUENCE: 7

Met Ala Gly Lys Lys Asn Val Leu Ser Ser Leu Ala Val Tyr Ala
1               5                   10                  15
```